United States Patent [19]

Valentine et al.

[11] Patent Number: 5,073,384

[45] Date of Patent: Dec. 17, 1991

[54] MALTODEXTRIN/DEFOAMING COMPOSITION COMBINATE

[75] Inventors: William Valentine; William K. Valentine, both of Lawrenceville, Ga.

[73] Assignee: Valentine Enterprises, Inc., Lawrenceville, Ga.

[21] Appl. No.: 423,877

[22] Filed: Oct. 19, 1989

[51] Int. Cl.$^5$ .................... A61K 9/28; A61K 9/14
[52] U.S. Cl. ................... 424/474; 424/452; 424/465; 424/469; 424/470; 424/489; 424/499; 424/724; 514/777; 514/960
[58] Field of Search ............... 424/474, 465, 469, 470

[56] References Cited

U.S. PATENT DOCUMENTS

| | | | |
|---|---|---|---|
| Re. 30,880 | 3/1982 | Armbruster | 435/99 |
| 2,441,098 | 9/1946 | Hyde | 260/607 |
| 2,774,710 | 12/1956 | Thompson et al. | 167/55 |
| 3,076,768 | 2/1963 | Boylan | 252/358 |
| 3,207,698 | 9/1965 | Liebling et al. | 252/321 |
| 3,304,266 | 2/1967 | Sullivan | 252/358 |
| 3,326,754 | 6/1967 | Prussin et al. | 167/55 |
| 3,388,073 | 6/1968 | Domba | 252/321 |
| 3,501,571 | 3/1970 | Yen | 424/157 |
| 3,663,369 | 5/1972 | Morehouse et al. | 195/31 |
| 3,691,091 | 9/1972 | Koerner | 252/358 |
| 3,705,859 | 12/1972 | Boylan | 252/321 |
| 3,714,068 | 1/1973 | Miller et al. | 252/358 |
| 3,746,653 | 7/1973 | Churchfield | 252/321 |
| 3,767,794 | 10/1973 | McVean et al. | 424/157 |
| 3,784,479 | 1/1974 | Keil | 252/358 |
| 3,843,558 | 10/1974 | Farminer et al. | 252/358 |
| 3,849,194 | 11/1974 | Armbruster et al. | 127/29 |
| 3,865,544 | 2/1975 | Keil | 8/93 |
| 3,909,445 | 9/1975 | Ernst | 252/321 |
| 3,912,652 | 10/1975 | Colquhoun | 252/358 |
| 3,959,176 | 5/1976 | Mahn et al. | 252/352 |
| 4,102,823 | 7/1978 | Matheson et al. | 252/533 |
| 4,115,553 | 9/1978 | Rubino et al. | 424/155 |
| 4,127,650 | 11/1978 | Buehler | 424/184 |
| 4,180,485 | 12/1979 | Llenado | 252/532 |
| 4,230,693 | 10/1980 | Izzo et al. | 424/156 |
| 4,264,465 | 4/1981 | Abel | 252/99 |
| 4,298,400 | 11/1981 | Armbruster | 127/29 |
| 4,386,106 | 5/1983 | Merritt et al. | 426/5 |
| 4,396,604 | 8/1983 | Mitra | 424/154 |
| 4,497,832 | 2/1985 | Cherukuri et al. | 426/5 |
| 4,514,319 | 4/1985 | Kulkarni et al. | 252/321 |
| 4,581,381 | 4/1986 | Morris et al. | 514/819 |
| 4,590,075 | 5/1986 | Wei et al. | 426/5 |
| 4,605,551 | 8/1986 | Buehler et al. | 424/38 |
| 4,684,534 | 8/1987 | Valentine | 427/3 |
| 4,698,264 | 10/1987 | Steinke | 428/402 |
| 4,804,543 | 2/1989 | Dokuzovic et al. | 426/3 |
| 5,004,595 | 4/1991 | Cherukuri et al. | 424/48 |

FOREIGN PATENT DOCUMENTS

| | | |
|---|---|---|
| 508856 | 1/1955 | Canada. |
| 213953 | 3/1987 | European Pat. Off. |
| 1166877 | 10/1969 | United Kingdom. |
| 1267482 | 3/1972 | United Kingdom. |

*Primary Examiner*—Thurman K. Page
*Assistant Examiner*—James M. Spear
*Attorney, Agent, or Firm*—DeLio & Associates

[57] ABSTRACT

A consumable antigas or antiflatulent composition is produced by combining a water soluble agglomerated maltodextrin and a fluid, nonaqueous, defoaming or antifoaming composition such as simethicone or silicone, mineral or other oils containing silica to form a granular mixture. The granular mixture may be prepared in a unit dose in granular form or as a compressed tablet or capsule.

36 Claims, No Drawings

MALTODEXTRIN/DEFOAMING COMPOSITION COMBINATE

BACKGROUND OF THE INVENTION

This invention relates to a composition whereby fluid, nonaqueous, defoaming or antifoaming compositions are prepared as relatively free flowing granular combinates by intermixing them with a low density, highly porous, generally spherical, water soluble maltodextrin to form adjuvant agglomerate combinates suitable for addition to products or processes wherever a rapid dispersion of the antifoaming or defoaming compound in an aqueous medium is indicated or desired.

The following listing and characterization of fluid, nonaqueous, antifoaming or defoaming compositions or compounds used in the practice of this invention is given to more precisely and particularly illustrate applicable compositions and compounds. The listing is not meant to limit or to specifically define the category of fluid, nonaqueous antifoaming or defoaming compositions, but rather to illustrate the scope of compositions applicable to the formation of the adjuvant agglomerate combinates.

Fluid hydrocarbon oil-based antifoaming or defoaming compositions containing a hydrocarbon-silicon copolymer, a hydrophobic filler, an organo-silicone surfactant, a hydrocarbon carrier oil, and, optionally, a silicone oil are disclosed in U.S. Pat. No. 4,514,319 to Kulcarni et al.

Fluid antifoaming or defoaming compositions comprising mineral oil-containing dispersed hydrophobic solid particles are well known in the art. The use of hydrophobic silica in fluid hydrocarbon oil based antifoam or defoaming composition is disclosed in U.S. Pat. Nos. 3,076,768; 3,207,698; 3,388,073; and 3,714,068.

Fluid antifoaming or defoaming compositions comprising polyoxyethylene-polypropylene copolymers containing dispersed hydrophobic silica are disclosed in U.S. Pat. Nos. 3,912,652 and 3,959,176.

Fluid antifoaming or defoaming compositions in a non-silicone oil and containing activated insitu hydrophobic silica particles are disclosed in U.S. Pat. No. 3,304,266.

Fluid antifoaming or defoaming compositions comprising a non-silicone water insoluble polyalkylene containing an alkoxysilicon chloride as the hydrophobic agent are disclosed in G.B. Patent No. 1,166,877.

Fluid antifoaming or defoaming compositions employing the use of other intrinsically hydrophobic fillers in organic liquids are also well known. For example, Canadian Patent No. 508,856 discloses N,N'-distearyl ethylene-diamide in white spirits, while the use of finely divided polyolefin polymers or polyesters dispersed in organic liquids is disclosed in U.S. Pat. No. 3,705,859. The use of fatty acid salts is disclosed in G.B. Patent No. 1,267,482 and low molecular weight polyethylenes in combination with mineral oil and conventional organic nonionic emulsifiers is disclosed in U.S. Pat. No. 3,909,445.

Fluid antifoam or defoaming compositions comprising silicone oil-silica compounds containing organo silicone compounds to improve performance are disclosed in U.S. Pat. No. 3,691,091.

Fluid antifoam or defoaming compositions comprising the use of silicone-glycol copolymers in association with silicone oil and silica are disclosed in U.S. Pat. Nos. 3,746,653; 3,784,479; and 3,865,544.

Simethecone is a fluid antifoam or defoaming composition comprised of polydimethylsiloxane and silica suitable purified for its intended application. The preparation of liquid methylsiloxane polymers is delineated in U.S. Pat. No. 2,441,098, the disclosure of which is hereby incorporated by reference. The normal physical state of the simethicone is a water white to grey translucent, viscous, oil-like liquid with a density of 0.965-0.970 grams/cubic centimeter having demonstrable immiscibility with water and alcohol.

The medically established therapeutic use for simethicone is as an ointment base ingredient, topical drug vehicle, skin protectant, but most particularly as an antigas and antiflatulent agent for human application as well as an antibloating agent for veterinary (animal) application. A combinate of simethicone and calcium silicate useful for such latter applications is disclosed in U.S. patent application No. 283,310 to Valentine et al.

Various antigas or antifoam formulations, some containing simethicone, are disclosed in the prior art. The pharmaceutical and medicinal applications include U.S. Pat. Nos. 4,605,551 to Buehler et al; 3,326,754 to Prussin et al; 2,774,710 to Thompson et al; 4,115,553 to Rubino et al; 4,396,604 to Mitra; 3,767,794 to McVean et al; and 4,581,381 to Morris et al. Non-pharmaceutical and non-medicinal antifoaming applications, such as powdered cleaning agents, are disclosed in U.S. Pat. Nos. 3,843,558 to Farminer et al; 4,180,485 to Llenado; 4,264,465 to Abel; 4,102,823 to Matheson et al; and European Patent 213,953 to Iley et al.

The preferred pharmaceutical solid dose delivery system for simethicone is a chewable tablet. Such chewable tablets often contain antacid ingredients such as calcium carbonate, aluminum hydroxide, magnesium hydroxide and magnesium carbonate. The article by F. Maksond et al, "Simethicone use in Antacid Medications" as published in *Manufacturing Chemist and Aerosol News*. Vol. 47, No. 5, 1976, pp 36-36 discloses instability problems when simethicone is intermixed with aluminum or magnesium bases. It is extremely troublesome to distribute the oil-like, viscous, water and alcohol immiscible simethicone expeditiously and uniformly throughout a tablet granulation prior to compression. It is equally difficult to be certain that the simethicone is in a sufficiently divided and dispersed state so that its action will be quick and effective when administered per os as a chewable or swallowable tablet or powder filled capsule.

Bearing in mind the problems and deficiencies of the prior art, it is therefore an object of the present invention to provide an improved combinate for dispersing antifoaming or defoaming compounds in an aqueous medium.

It is another object of the present invention to provide an effective simethicone containing granule for use in gastric antacid, antigas, and/or antiflatulent formulations.

It is a further object of the present invention to provide granules to be added to aqueous based products or processes wherever antifoaming or defoaming is indicated or desired.

It is yet another object of the present invention to provide a facile method of producing an effective simethicone-containing foam controlling granule utilizing conventional equipment at relatively low cost.

It is a further object of the present invention to provide a free flowing simethicone containing granule for use in conventional formulations which, after processing, retains acceptable defoaming activity.

It is yet another object of the present invention to provide an antifoaming or defoaming compound combinate which retains its properties and activity after extended storage and at elevated temperatures.

The present invention achieves these objects and satisfies the long felt need to overcome the difficulties in expeditious utilization of antifoaming or defoaming compounds in an aqueous medium. A larger amount of antifoaming or defoaming compound can be incorporated with the maltodextrin agglomerate of this invention for dispersion than has previously been disclosed in the prior art. The water solubility of the maltodextrin portion of the combinate makes it possible to effect rapid and uniform distribution of the antifoaming-/defoaming compound by simple mixing.

SUMMARY OF THE INVENTION

The present invention relates to fluid, nonaqueous, antifoaming or defoaming compounds prepared as a flowable granule by intermixing a fluid, nonaqueous, antifoaming or defoaming compound or composition and a low density, highly porous, generally spherical, water soluble, maltodextrin agglomerate to form a functional combinate. Maltodextrin is a low conversion starch hydrolyzate having a D. E. (dextrose equivalent) less than 20. The fluid, nonaqueous, antifoaming or defoaming compound or composition is added, in liquid form, to agglomerated maltodextrin and blended to form a uniform, relatively free flowing combinate in which the base structure is water soluble. The combinate may be readily added to conventional products and processes where a rapid dispersion of the fluid, nonaqueous, antifoaming or defoaming compound is indicated. It is preferred that the fluid, nonaqueous, antifoaming or defoaming combinate have from about 10 to 50 weight percent antifoaming or defoaming composition or compound, and from about 90 to 50 weight percent maltodextrin. It is more preferred that the fluid, nonaqueous, antifoaming or defoaming composition or compound represents 30 weight percent and the water soluble, highly porous, low density, generally spherical, msltodextrin agglomerate represents 70 weight percent of the admixture combinate. The terms þantifoaming? and "defoaming" are generally used interchangably throughout the specification. The antifoaming compositions or compounds useful in this invention may be any of those discussed in the background section of the specification, particularly simethicone (for pharmaceutical and medicinal applications) and silicone, mineral or other oils containing silica.

DETAILED DESCRIPTION OF THE INVENTION

The preferred fluid, nonaqueous, antifoaming or defoaming compound prepared as a flowable granule used herein is simethicone and, more specifically, simethicone U.S.P. as defined in the United States Pharmacopeia, incorporated herein by reference, which has the chemical structure:

and the chemical formula:
Alpha(trimethylsilyl)-omega-methylpoly[oxy (dimethylsilylene)] in mixture with silicon dioxide.

Simethicone is a mixture of fully methylated linear siloxane polymers containing repeating units of the formula $[—(CH_3)_2\,SiO—]_n$, stabilized with trimethylsilyloxy end-blocking units of the formula $[(CH_3)_3SiO—]$, and silicon dioxide. It is preferred to contain not less than 90.5 percent and not more than 99.0 percent of polydimethylsiloxane $([—(CH_3)_2\,SiO—]_n)$, and not less than 4.0 percent and not more than 7.0 percent of silicon dioxide.

Maltodextrins are composed of water soluble glucose polymers obtained from the reaction of starch with acid and/or enzymes in the presence of water. The starch is hydrolyzed to produce hydrolyzate products containing sugars. The production of starch hydrolyzates, and, in particular, low conversion starch hydrolyzates, is described in U.S. Pat. Nos. 3,663,369; 3,849,194; 4,298,400; and Re. 30,880, the disclosures of which are hereby incorporated by reference. The starch used for the preparation of maltodextrins can be any of a variety of commercially available starches such as maize, potato, or tapioca. Further, the United States Food and Drug Administration defines maltodextrins, $(C_6H_{12}O_5)_nH_2O$, as nonsweet nutritive saccharide polymers that consist of D-glucose units linked primarily by alpha 1–4 bonds and having a D.E. (total reducing sugars expressed as dextrose equivalents) of less than 20.

Maltodextrin is usually produced as a fine, white powder and is generally recognized as safe (gras) as a direct human food ingredient at levels consistent with good manufacturing practices. Agglomerated maltodextrin is available from a variety of commercial sources and in a larger, more porous, faster dissolving, and more free flowing form.

The preferred commercial source for low density, highly porous, generally spherical, water soluble maltodextrin agglomerates is the product family sold by Valentine Enterprises, Inc. of Lawrenceville, Ga. under the trademark VELite. The preferred VELite is VELite 2000 20/40 which is prepared from 9–12 D.E. maltodextrin, derived from corn starch, and having the following typical analysis: a particle size distribution of 100 percent less than 850 microns and a majority (98 percent) greater than 420 microns; an apparent density, of from about 10 to about 12 pounds per cubic foot; a maximum moisture content of 6 percent; and a total surface area of between about 9.5±1 and 10.5±1 square meters per gram as determined by a 3 point nitrogen B.E.T. analysis.

A preferred embodiment of the present invention is directed toward the admixture of simethicone and maltodextrin agglomerate to form a uniform, relatively free flowing, granular combinate containing 30 percent by weight of simethicone and 70 percent by weight maltodextrin for incorporation into tablets or for use "as is" for addition to an aqueous medium whenever antifoaming or defoaming is desired.

The 30 percent by weight simethicone/70 percent by weight agglomerated maltodextrin combinate is readily formulated into, for example, antacid or antigas formulations by adding the 30% simethicone active granule combinate to a compressible granule base without sacrificing or compromising the compressibility of the base granule. It is a further feature of the present invention that the simethicone is contained in or on a water soluble agglomerated maltodextrin and, as such, is available and stable in the formulations.

The art of the present invention may be practiced by obtaining desired quantities of agglomerated maltodextrin, such as VELite 2000 20/40 available from Valentine Enterprises, Inc., and consumable simethicone, such as Sentry simethicone available from Union Carbide Corporation. These two starting materials are then mixed employing low shear mixing such as that encountered in a planetary, ribbon or plow mixer in order to effect a uniform combinate agglomerate suitable for use without further processing.

The relative amounts of the simethicone and the maltodextrin agglomerate may range from about 10 to about 50 weight percent simethicone and from about 90 to about 50 percent by weight of agglomerated maltodextrin. This range of the ingredients has been found to provide optimum performance of the final simethicone/agglomerated maltodextrin combinate. If more than about 50% by weight percent simethicone is used, the product tends to be too moist and exhibits poor flow. If more than 90% by weight of agglomerated maltodextrin is used the product tends to exhibit non-uniform distribution of the simethicone. Exceeding either extreme will tend to result in poor product performance, most particularly in final tableting. A 30% by weight simethicone to 70% by weight agglomerated maltodextrin ratio represents the preferred product performance whether for tableting or for general purpose aqueous antifoaming or defoaming application.

The combinate maltodextrin and the antifoaming or defoaming composition preferably has a particle size in which essentially all of the particles are less than about 20 mesh (−20 mesh) and greater than 40 mesh (+40 mesh) and a total typical surface area of less than about 1 square meter per gram.

While not wishing to be limited to a particular combinate formation theory, it is believed that sorption, i.e., absorption or adsorption, takes place during the blending whereupon the liquid simethicone or other defoaming compound or composition (the sorbate) is taken up by the agglomerated maltodextrin (the sorbent). It is further theorized that the rapid water solubility of the maltodextrin moiety of the combinate helps to explain the speed of action of the product since the simethicone or other defoaming compound is liberated in dispersed particles.

The antifoaming and/or defoaming containing adjuvant combinate granules of the present invention have been found to be equal in foam inhibition and foam breaking to an equivalent quantity of the starting simethicone. This means, for example, that 66.7 mg of the 30% simethicone combinate granule is equivalent in performance to 20 mg of simethicone. The equivalent performance is demonstrable even after the simethicone/agglomerated maltodextrin combinates have been stored at 45° C. for a period of two months.

Defoaming activity of the simethicone/agglomerated maltodextrin combinate or of the monadic simethicone or of the simethicone/agglomerated maltodextrin combinate contained as part of an antacid and/or antigas tablet, i.e., foam breaking (defoaming) and/or foam inhibition (antifoaming), may be defined and measured by the procedure given in the United States Pharmacopeia. First, a foaming solution and test preparation are prepared as follows:

Foaming solution—dissolve 1 g of octoxylnol 9 in 100 ML of distilled water.

Test preparation—transfer 200 mg of simethicone to a 60 ml bottle, add 50 ml of tertiary butyl alcohol, cap the bottle, and shake vigorously. The preparation may be warmed slightly, if necessary, to effect the solution.

The procedure for determining defoaming activity as follows: For each test, a clean, unused 250 ml glass jar fitted with a 50 mm cap should be employed. Add, dropwise, 0.5 ml of the test preparation (i.e., equivalent to 2.0 mg simethicone) to the 250 ml glass jar containing 100 ml of the foaming solution. Cap the jar and clamp it in an upright position on a wrist action shaker. Employing a radius of 13.3±0.4 cm (measured from the center of the shaft to the center of the bottle), shake for 10 seconds through an arc of 10° at a frequency of 300±30 strokes per minute. Record the time required for the foam to collapse. The time, in seconds, for foam collapse is determined at the instant the first portion of foam-free liquid surface appears, measured from the end of the shaking period. This time is the defoaming activity time and should not exceed 15 seconds for acceptable simethicone activity. To evaluate the simethicone/maltodextrin agglomerate combinate activity, a quantity of the combinate equivalent to 2.0 mg of simethicone (i.e. 6.7 mg of a 30% simethicone/ maltodextrin combinate) is introduced directly into the test solution and the defoaming time is determined as described above.

There is no fixed quantity of simethicone, supplied by the simethicone maltodextrin combinate, which must be used to prepare an antacid/antigas preparation. A typical formulation would contain:
Aluminum hydroxide dried gel 200 mg
Magnesium hydroxide, dried 200 mg
Simethicone/maltodextrin combinate 85 mg Not only will the simethicone/maltodextrin agglomerate release the simethicone by virtue of the water solubility of the maltodextrin moiety, but, when the combinate is added to tablet granulations, no deleterious compression effects are evidenced. Whether or not the foam inhibition attributes of the simethicone/maltodextrin agglomerate combinates are measured from the combinate alone or combined with standard antacid ingredients, in tablet or granule form, defoaming results are obtained which are equivalent to simethicone alone. Significantly, the same defoaming test results are evidenced even after accelerated storage stability at 37° C., and 60° C., for periods up to 2 months.

Therefore, the simethicone/agglomerated maltodextrin adjuvant combinate demonstrates itself as a uniquely stable product capable of being combined with antacid ingredients such as aluminum and magnesium bases in a single layer tablet without compromising the acid neutralizing or the defoaming or antifoaming capacity of the dose form.

Standard excipients can be combined with the simethicone/agglomerated maltodextrin combinate granules in order to prepare pharmaceutical preparations in the form of tablets or capsules. In order to prepare tablets, the simethicone/agglomerated maltodextrin combinate may be combined and blended with standard compression granules comprising, for example, calcium carbonate, dextrose, sucrose, mannitol, sorbitol, aluminum hydroxide dried gel, magnesium hydroxide, any compatible spray dried flavor, and magnesium stearate. The blended preparation may be pressed by standard, well known techniques to form tablets of desired weight, potency, and hardness. A single layer homogeneous unit dosage tablet or capsule may preferably contain from about 80 mg to about 280 mg of the simethicone/agglomerated maltodextrin combinate (i.e., from about 25 to about 80 mg of simethicone), but any desired amount outside this range may be used for specific applications.

The maltodextrin/defoaming composition or compound combinate of the present invention may be used by contacting the aqueous medium in which defoaming is desired with the combinate. In the case of simethicone for use in pharmaceutical or medicinal applications, the maltodextrin/simethicone combinate would be ingested by the user in tablet, capsule, granule or other unit dose form to provide antigas and/or antiflatulent treatment. In the case of other defoaming compositions or compounds, the combinate may be prepared as granules in bulk filled packages or in unit dose forms such as compressed tablets or water soluble pouches for application to the aqueous medium.

Acid neutralizing capacity may be measured by the procedure set forth in the United States Pharmacopeia. The analytical procedure, to be conducted at 37° C.±3° C., is as follows:

First, standardize a pH meter using 0.05M potassium biphthalate and 0.05M potassium tetraoxalate standardizing buffers. Next, transfer 100 ml of water to a 250 ml beaker containing a 40×10 mm magnetic stirring bar that is coated with solid perfluorocarbon and has a spin ring at its center. The power setting of the magnetic stirrer should be adjusted to produce a stirring rate of 300 rpm when the stirring bar is centered in the beaker, as determined by a suitable optical tachometer.

The test preparations are prepared as follows:

powders—transfer the accurately weighed portion of the substance to be tested to a 250 ml beaker, add 70 ml of water, and mix in the magnetic stirrer for one minute.

Tablets—weigh not less than 20 tablets and determine the average tablet weight Grind the tablets to a powder that passes through a no. 20 sieve and is retained on a 100 sieve. Mix the material on the no. 100 sieve to obtain a uniform mixture, transfer an accurately weighed quantity of it, equivalent to the minimum dosage, to a 250 ml beaker. If wetting is desired, add not more than 5ml of alcohol (neutralized to an apparent pH of 3.5), and mix to wet the specimen thoroughly. Add 70 ml of water, and mix on the magnetic stirrer for one minute.

The test procedure is as follows: Pipet 30.0 ml of 0.0N hydrochloric acid vs into the test preparation prepared earlier while continuing to stir with the magnetic stirrer. Magnetic stirring should continue for 15 minutes (accurately timed) after the addition of the acid. Thereafter, begin to titrate immediately, in a period not to exceed 5 minutes, the excess hydrochloric acid with 0.5N sodium hydroxide vs to attain a stable pH of 3.5 for not less than 15 seconds. Calculate the number of mEq of acid consumed per gram of the substance tested. Each ml of 1.0N hydrochloric acid is equal to 1 mEq of acid consumed.

EXAMPLES

The following illustrative examples are given to more precisely and particularly illustrate the specific details of the present invention. Equivalent procedures and quantities will occur to those skilled in the art and therefore, the following examples are not meant to define the limits of the present invention, these being defined by the scope of the appended claims.

EXAMPLE 1

| Starting Materials: | |
|---|---|
| Simethicone U.S.P. (Sentry simethicone) | 40 g |
| Agglomerated Maltodextrin (VELite 2000 20/40) | 160 g |

The VELite 2000 20/40 was charged into a 1000 cc stainless steel beaker and the simethicone was added. The total materials were blended with a spatula until uniform. The resulting granular combinate was lump free, less than 850 microns (20 mesh) in size, and contained 20% simethicone.

A portion of the sample was used to prepare chewable antacid tablets containing 125 mg of the simethicone/agglomerated maltodextrin combinate per tablet (equivalent to 25 mg of simethicone per tablet).

EXAMPLE 2

| Starting materials: | |
|---|---|
| Simethicone U.S.P. (Sentry simethicone) | 300 g |
| Agglomerated maltodextrin (VELite 2000 20/40) | 700 g |

The VELite 2000 20/40 was charged into a 5000 ml stainless steel beaker and the simethicone was added. The total materials were blended with a spatula until uniform. The resulting granular combinate was lump free, less than 850 microns (20 mesh) in size and contained 30% simethicone.

A portion of the sample was used to prepare chewable antacid tablets containing 84 mg of the simethicone/agglomerated maltodextrin combinate per tablet (equivalent to 25 mg simethicone per tablet).

EXAMPLE 3

| Starting materials: | |
|---|---|
| Simethicone U.S.P. (Sentry simethicone) | 400 g |
| Agglomerated maltodextrin (VELite 2000 20/40) | 600 g |

VELite 2000 20/40 was charged into a 5000 ml stainless steel beaker and the simethicone was added. The total materials were blended with a spatula until uniform. The resulting granular combinate was lump free, less than 850 microns (20 mesh) in size and contained 40% simethicone.

A portion of the sample was used to prepare chewable antacid tablets containing 63 mg of the simethicone/agglomerated maltodextrin combinate per tablet (equivalent to 25 mg of simethicone per tablet).

EXAMPLE 4

| Starting materials: | |
|---|---|
| Simethicone U.S.P. (Sentry simethicone) | 1.5 kg |
| Agglomerated maltodextrin (VELite 2000 20/40) | 3.5 kg |

VELite 2000 20/40 was charged into a 5 gallon stainless steel Hobart mixer and the simethicone was added. The mixer was energized and mixing was effected for a period of 10 minutes. The resulting granular combinate was found to be lump free, less than 850 microns (20 mesh) in size, and contained 30% simethicone.

A portion of the product was used to prepare chewable antacid tablets containing 84 mg of the simethicone/agglomerated maltodextrin combinate per tablet (equivalent to 25 mg of simethicone per tablet).

EXAMPLE 5

| Starting materials: | |
|---|---|
| Simethicone U.S.P. (Sentry simethicone) | 30 kg |
| Agglomerated maltodextrin (VELite 2000 20/40) | 70 kg |

VELite 2000 20/40 was charged into a 20 cubic foot capacity ribbon blender and the simethicone was added. The mixer was energized and mixing was effected for a period of 10 minutes. The resulting granular combinate was discharged into drums and found to be lump free, less than 850 microns (20 mesh) in size, and contained 30% simethicone.

A portion of the product was used to prepare chewable antacid tablets containing 84 mg of the simethicone/agglomerated maltodextrin combinate per tablet (equivalent to 25 mg of simethicone per tablet).

EXAMPLE 6

| Starting materials: | |
|---|---|
| Simethicone U.S.P. (Sentry simethicone) | 3.0 kg |
| Agglomerated maltodextrin (VELite 2000 20/40) | 7.0 kg |

VELite 2000 20/40 was charged into a 3 cubic foot capacity stainless steel Lodige blender and the simethicone was added. The plow blades of the mixer were energized and mixing effected for a period of 10 minutes. The resulting granular combinate was discharged into a drum and found to be lump free, less than 850 microns (20 mesh) in size, and contained 30% simethicone.

A portion of the product was used to prepare chewable antacid tablets containing 84 mg of the simethicone/agglomerated maltodextrin combinate per tablet (equivalent to 25 mg of simethicone per tablet).

EXAMPLE 7

| Starting materials: | |
|---|---|
| Simethicone U.S.P. (Sentry simethicone) | 90 kg |
| Agglomerated maltodextrin (VELite 2000 20/40) | 210 kg |

VELite 2000 20/40 was charged into a 1200 l stainless steel Lodige blender and the simethicone added. The plow blades of the mixer were energized an mixing was effected for a period of 10 minutes. The resulting granular combinate was discharged into drums and found to be lump free, less than 850 microns (20 mesh) in size, and contained 30% simethicone.

A portion of the product was used to prepare chewable antacid tablets containing 84 mg of the simethicone/agglomerated maltodextrin combinate per tablet (equivalent to 25 mg of simethicone per tablet).

EXAMPLE 8

Each of the simethicone/maltodextrin combinates produced in Examples 1-7 were evaluated in the following manner:

A quantity of the simethicone/agglomerated maltodextrin combinates were evaluated in the standard U.S.P. defoaming test at a level equivalent to 2 mg of simethicone.

| Example No. | Quantity of the Combinate Used (mg) | Simethicone Equivalent (mg) | Time to Defoam (sec.) |
|---|---|---|---|
| 1 | 10.0 | 2 | 3-4 |
| 2 | 6.7 | 2 | 3-4 |
| 3 | 5.0 | 2 | 3-4 |
| 4 | 6.7 | 2 | 3-4 |
| 5 | 6.7 | 2 | 3-4 |
| 6 | 6.7 | 2 | 3-4 |
| 7 | 6.7 | 2 | 3-4 |
| Controls | | | |
| Simethicone U.S.P | 2.0 | 2 | 3-4 |
| Simethicone U.S.P (as 30% emulsion) | 6.7 | 2 | 3-4 |

The data suggests that equivalent quantities of simethicone derived from either the simethicone/ maltodextrin combinates or from the Simethicone U.S.P. or from the commercial 30% silicone emulsion demonstrate equivalent defoaming action.

Stability samples stored for periods up to 2 months at 37° C. and 45° C. evidence no change in defoaming times and are unchanged in physical appearance.

It is observed that when the simethicone/agglomerated maltodextrin combinates (Examples 1-7) are added to water at a level calculated to liberate 100 mg of simethicone, the maltodextrin moiety dissolves in the water and the silicone forms a surface oil layer.

EXAMPLE 9

Each of the simethicone/agglomerated maltodextrin combinates produced in Examples 1-7 were evaluated in a typical chewable antacid tablet formulation as follows (all values in mg):

| | EX. 1 | EX. 2 | EX. 3 | EX. 4 | EX. 5 | EX. 6 | EX. 7 |
|---|---|---|---|---|---|---|---|
| Compression Dextrose | 661 | 702 | 723 | 702 | 702 | 702 | 702 |
| Aluminum Hydroxide Dried Gel | 200 | 200 | 200 | 200 | 200 | 200 | 200 |
| Magnesium Hydroxide Powder | 200 | 200 | 200 | 200 | 200 | 200 | 200 |
| Simethicone/ Maltodextrin | 125 | 84 | 63 | 84 | 84 | 84 | 84 |

-continued

|  | EX. 1 | EX. 2 | EX. 3 | EX. 4 | EX. 5 | EX. 6 | EX. 7 |
|---|---|---|---|---|---|---|---|
| Combinate Equivalent to 25 mg of Simethicone |  |  |  |  |  |  |  |
| Spray Dried Flavor | 5 | 5 | 5 | 5 | 5 | 5 | 5 |
| Magnesium Stearate | 9 | 9 | 9 | 9 | 9 | 9 | 9 |

Each of the formulations were produced as single layer 9/16 inch, flat-faced, beveled edge chewable tablets, compressed at a weight of 1200 mg and a hardness of 7-9 Kp. Tablets without simethicone were also produced under the same conditions to serve as a control.

All of the tablets produced for the trials satisfied the criteria for taste acceptance, mouth feel, hardness, friability, and acid neutralization.

Each of the tablet formulations were evaluated for defoaming in accordance with the U.S.P. method for antacid tablets with the following results:

| Tablets produced with Simethicone/Maltodextrin Combinate From: | Test Storage Condition: | |
|---|---|---|
|  | Initial Time to Defoam (In Seconds) | 45° for 2 Months Time to Defoam (In Seconds) |
| EX. 1 | 5-7 | 5-7 |
| EX. 2 | 5-7 | 5-7 |
| EX. 3 | 5-7 | 5-7 |
| EX. 4 | 5-7 | 5-7 |
| EX. 5 | 5-7 | 5-7 |
| EX. 6 | 5-7 | 5-7 |
| EX. 7 | 5-7 | 5-7 |
| Control | No Defoaming | No Defoaming |

After storage at 45° C. for a period of two months all of the tablets still satisfied the acid neutralization criteria for extra strength antacid tablets.

EXAMPLE 10

Calcium carbonate-based antacid tablets were prepared with and without simethicone/agglomerated maltodextrin combinate as follows (all values in mg):

| Formula: | With Combinate | Without Combinate |
|---|---|---|
| Calcium Carbonate Compression Granules (53% Calcium Carbonate 47% Dextrose) | 1000 | 1000 |
| Compression Dextrose | 104 | 188 |
| Simethicone/Agglomerated Maltodextrin Combinate From Example #7 | 84 | — |
| Spray Dried Flavor | 3 | 3 |
| Magnesium Stearate | 9 | 9 |

Each of the formulations were processed into single layered 9/16 inch, flat faced, beveled edge chewable tablets compressed at a weight of 1200 mg and a hardness of 7-9 Kp.

Each of the chewable tablet formulations produced for the trials satisfied the criteria for chewable tablets with respect to taste acceptance, mouth feel, hardness, friability, and acid neutralization.

Each of the chewable tablet formulations were evaluated for defoaming in accordance with the U.S.P. method for antacid tablets with the following results:

|  | Defoaming Time |
|---|---|
| Formulation With Combinate | 4-6 sec. |
| Formulation Without Combinate | No Defoaming |

EXAMPLE 11

Magaldrate (aluminum magnesium hydrate with magnesium sulfate) based antacid tablets were prepared with and without simethicone/agglomerated maltodextrin combinate as follows (all values in mg):

| Formula | With Combinate | Without Combinate |
|---|---|---|
| Dextrose Compression Granules | 702 | 786 |
| Magaldrate | 400 | 400 |
| Simethicone/Agglomerated Maltodextrin Combinate From Example 7 | 84 | — |
| Spray Dried Flavor | 5 | 5 |
| Magnesium Stearate | 9 | 9. |

Both of the formulations were processed into single layered 9/16 inch, flat-faced, beveled edge chewable antacid tablets at a weight of 1200 mg and a hardness of 7-9 Kp.

The chewable antacid tablets produced for the trials, i.e., with and without the simethicone/agglomerated maltodextrin combinate, satisfied the criteria for taste acceptance, mouth feel, hardness, friability, and acid neutralization.

Each of the formulations were evaluated for defoaming in accordance with the U.S.P. method for antacid tablets with the following results:

|  | Defoaming Time |
|---|---|
| Formulation With Combinate | 4-6 sec. |
| Formulation Without Combinate | No Defoaming |

EXAMPLE 12

An antigas chewable tablet formulation was prepared to demonstrate the utility of simethicone/agglomerated maltodextrin combinate in such an application as follows (all values in mg):

| Compression Dextrose | 946 |
|---|---|
| Simethicone/Agglomerated Maltodextrin Combinate From Example 7 | 240 |
| Spray Dried Flavor | 5 |
| Magnesium Stearate | 9. |

The formulation was produced as a single layered 9/16 inch, flat-faced, beveled edged chewable tablet compressed at a weight of 1200 mg and a hardness of 7-9 Kp.

The tablets produced satisfied the criteria for taste acceptance, mouth feel, hardness, friability, and foam suppression.

EXAMPLE 13

To further illustrate the utility of the invention, a general standard fluid silicone oil defoamer/agglomerated maltodextrin combinate was prepared:

| Starting Materials Used: | |
|---|---|
| Fluid Silicone Oil Containing Silica | 1.05 kg |
| Agglomerated Maltodextrin (VELite 2000 20/40) | 2.45 kg |

The VELite 2000 20/40 was charged into a 5 gallon stainless steel Hobard mixer and the fluid silicone oil containing silica added. The mixer was energized and mixing was effected for a period of 10 minutes. The resulting granular combinate was lump free, less than 850 microns (20 mesh) in size and contained 30% of the fluid silicone oil containing silica defoaming compound.

The above described combinate demonstrated satisfactory antifoaming/defoaming properties when subjected to the standard U.S.P. defoaming test.

EXAMPLE 14

To further illustrate the utility of the invention, a general standard fluid mineral oil defoamer/agglomerated maltodextrin combinate was prepared as follows:

| Starting Materials Used: | |
|---|---|
| Fluid Mineral Oil Containing Silica | 1.05 kg |
| Agglomerated Maltodextrin (VELite 2000 20/40) | 2.45 kg |

The VELite 2000 20/40 was charged into a 5 gallon stainless steel Hobard mixer and the fluid mineral oil containing silica added. The mixer was energized and mixing was effected for a period of 10 minutes. The resulting granular combinate was lump free, less than 850 microns (20 mesh) in size and contained 30% of the fluid silicone oil containing silica defoaming compound.

The above described combinate demonstrated satisfactory antifoaming/defoaming properties when subjected to the standard U.S.P. defoaming test.

While the invention has been described with reference to specific embodiments, it will be recognized by those skilled in the art that variations are possible without departing from the spirit and scope of the invention, and that it is intended to cover all changes and modifications of the invention disclosed herein for the purposes of illustration which do not constitute departure from the spirit and scope of the invention.

Having thus described the invention, what is claimed is:

1. An antifoaming or defoaming composition comprising a uniform, free flowing granular combinate of at least about 50 weight percent water soluble agglomerated maltodextrin having a particle size of less than 850 microns and simethicone in an amount up to about 50 weight percent.

2. The composition of claim 1 wherein said simethicone is taken up by the agglomerated maltodextrin particles by sorption.

3. The composition of claim 1 wherein said combinate is comprised of 9-12 D.E. agglomerated maltodextrin having a particle size of less than about 850 microns with a majority greater than about 420 microns, a bulk density of from about 10 to about 12 pounds per cubic foot, and a total surface area of from about 9.5±1 square meters per gram to about 10.5±1 square meters per gram, and simethicone U.S.P.

4. The composition of claim 1 wherein said combinate further includes one or more excipients.

5. The composition of claim 1 comprising about 50 to 90 weight percent agglomerated maltodextrin and about 10 to 50 weight percent simethicone.

6. An antigas, antiflatulent or liquid defoaming compositions comprising a uniform, granular combinate of at least about 50 weight percent water soluble agglomerated maltodextrin having a particle size of less than 850 microns with a majority greater than about 420 microns and simethicone in an amount up to about 50 weight percent.

7. The composition of claim 6 wherein said simethicone is taken up by the agglomerated maltodextrin particles by sorption.

8. The composition of claim 6 wherein said agglomerated maltodextrin has a Dextrose Equivalent of 9 to 12, a bulk density of from about 10 to about 12 pounds per cubic foot, and a total surface area of from about 9.5±1 square meters per gram to about 10.5±1 square meters per gram.

9. The composition of claim 6 comprising about 50 to 90 weight percent agglomerated maltodextrin and about 10 to 50 weight percent simethicone.

10. The composition of claim 6 wherein said combinate further includes one or more excipients.

11. The composition of claim 6 wherein said combinate is prepared as a unit dose compressed tablet, capsule, or granule.

12. The composition of claim 6 further including one or more excipients and wherein said combinate is prepared as a bulk filled package or in a unit dose form.

13. The composition of claim 6 wherein said combinate is comprised of about 30 weight percent simethicone and about 70 weight percent agglomerated maltodextrin.

14. A process for producing an antifoaming or defoaming combinate comprising mixing at least about 50 weight percent water soluble agglomerated maltodextrin having a particle size of less than 850 microns with simethicone in an amount up to about 50 weight percent to form a uniform, free flowing granular combinate.

15. The process of claim 14 wherein said simethicone is taken up by the agglomerated maltodextrin particles by sorption.

16. The process of claim 14 wherein said agglomerated maltodextrin has a particle size of less than about 850 microns with a majority greater than about 420 microns, a Dextrose Equivalent of 9-12, a bulk density of from about 10 to about 12 pounds per cubic foot, and a total surface area of from about 9.5±1 square meters per gram to about 10.5±1 square meters per gram.

17. The process of claim 14 further including the step of blending one or more excipients with said combinate.

18. The process of claim 14 comprising mixing about 50 to 90 weight percent agglomerated maltodextrin and about 10 to 50 weight percent simethicone.

19. The process of claim 17 further including the step of preparing said combinate as a unit dose compressed tablet, capsule, or granule.

20. The process of claim 14 wherein said agglomerated maltodextrin has a particle size of less than about 850 microns with a majority greater than about 420 microns.

21. The process of claim 20 further including the steps of blending one or more excipients with said combinate and preparing said combinate in a unit does form.

22. A method of defoaming an aqueous medium comprising contacting said aqueous medium with an antifoaming or defoaming composition comprising a uniform granular combinate of at least about 50 weight percent water soluble agglomerated maltodextrin having a particle size of less than 850 microns and simethicone in an amount up to about 50 weight percent.

23. The method of claim 22 wherein said antifoaming or defoaming composition is taken up by the agglomerated maltodextrin particles by sorption.

24. The method of claim 22 wherein said combinate is comprised of 9-12 D.E. agglomerated maltodextrin having a particle size of less than about 850 microns with a majority greater than about 420 microns, a bulk density of from about 10 to about 12 pounds per cubic foot, and a total surface area of from about $9.5 \pm 1$ square meters per gram to about $10.5 \pm 1$ square meters per gram, and simethicone U.S.P.

25. The method of claim 22 wherein said combinate is comprised of about 50 to 90 weight percent agglomerated maltodextrin and about 10 to 50 weight percent simethicone.

26. The method of claim 22 wherein said combinate further includes one or more excipients.

27. The method of claim 22 wherein said agglomerated maltodextrin has a particle size of less than about 850 microns with a majority greater than about 420 microns.

28. The method of claim 27 wherein said combinate further includes one or more excipients.

29. The method of claim 22 wherein said combinate is in the form of a unit dose compressed tablet, capsule, or free flowing granules.

30. An antigas or antiflatulent treatment method comprising ingesting a unit dose of an antifoaming or defoaming composition comprising a uniform, granular combinate of at least about 50 weight percent water soluble agglomerated maltodextrin having a particle size of less than 850 microns and simethicone in an amount up to about 50 weight percent.

31. The method of claim 30 wherein said antifoaming or defoaming composition is taken up by the agglomerated maltodextrin particles by sorption.

32. The method of claim 30 wherein said combinate is comprised of 9-12 D.E. agglomerated maltodextrin having a particle size of less than about 850 microns with a majority greater than about 420 microns, a bulk density of from about 10 to about 12 pounds per cubic foot, and a total surface area of from about $9.5 \pm 1$ square meters per gram to about $10.5 \pm 1$ square meters per gram, and simethicone U.S.P.

33. The method of claim 30 wherein said combinate is comprised of about 50 to 90 weight percent agglomerated maltodextrin and about 10 to 50 weight percent simethicone.

34. The method of claim 30 wherein said combinate further includes one or more excipients.

35. The method of claim 30 wherein said agglomerated maltodextrin has a particle size of less than about 850 microns with a majority greater than about 420 microns.

36. The method of claim 35 wherein said combinate further includes one or more excipients.

* * * * *

UNITED STATES PATENT AND TRADEMARK OFFICE
CERTIFICATE OF CORRECTION

PATENT NO. : 5,073,384

DATED : December 17, 1991

INVENTOR(S) : William Valentine and William K. Valentine

It is certified that error appears in the above-identified patent and that said Letters Patent is hereby corrected as shown below:

Column 7, line 47, delete "0.0N" and substitute therefor --1. 0 N--.

Signed and Sealed this

Twenty-seventh Day of April, 1993

Attest:

MICHAEL K. KIRK

Attesting Officer

Acting Commissioner of Patents and Trademarks